_United States Patent_ [19]

Aggarwal et al.

[11] Patent Number: 5,981,583
[45] Date of Patent: *Nov. 9, 1999

[54] INHIBITION OF NUCLEAR TRANSCRIPTION FACTOR NF-κB BY CAFFEIC ACID PHENETHYL ESTER (CAPE), DERIVATIVES OF CAPE, CAPSAICIN (8-METHYL-N-VANILLYL-6-NONENAMIDE) AND RESINIFERATOXIN

[75] Inventors: Bharat B. Aggarwal, Houston, Tex.; Dezider Grunberger, Teaneck, N.J.

[73] Assignee: Research Development Foundation, Carson City, Nev.

[ * ] Notice: This patent issued on a continued prosecution application filed under 37 CFR 1.53(d), and is subject to the twenty year patent term provisions of 35 U.S.C. 154(a)(2).

[21] Appl. No.: 08/924,365

[22] Filed: Sep. 5, 1997

Related U.S. Application Data

[60] Provisional application No. 60/024,602, Sep. 5, 1996, abandoned.

[51] Int. Cl.[6] .......................... A01N 37/10; A01N 37/00; C07C 69/76
[52] U.S. Cl. ............................. 514/532; 514/557; 560/75
[58] Field of Search ..................... 514/532, 533, 514/921, 914, 548, 557; 560/75

[56] References Cited

U.S. PATENT DOCUMENTS

| | | | |
|---|---|---|---|
| 5,008,441 | 4/1991 | Nakanishi et al. ........................ | 560/75 |
| 5,021,450 | 6/1991 | Blumberg ................................ | 514/453 |
| 5,290,816 | 3/1994 | Blumberg ................................ | 514/691 |
| 5,591,773 | 1/1997 | Grunberger et al. ................... | 514/532 |

OTHER PUBLICATIONS

Deal et al. "Treatment of arthrtis with topical capsaicin: A double–blind trial," Clin. Ther. (1991) 13(3):383–395.

Natarajan et al. "Caffeic acid phenethyl ester is a potent and specific inhibitor of activation of nuclear transcription factor NF–.kappa.B," Proc. Natl. Acad. Sci. USA (Aug. 1996) 93: 9090–5.

Singh et al. "Activation of transcription factor NK–.kappa.B is suppressed by curcumin (diferulolymethane)," J. Biol. Chem. (Oct. 1995) 270(42): 24995–25000.

_Primary Examiner_—Jean C. Witz
_Assistant Examiner_—Susan Hanley
_Attorney, Agent, or Firm_—Benjamin Aaron Adler

[57] ABSTRACT

The present invention is drawn to the inhibition of activation of NF-κB by caffeic acid phenethyl ester (CAPE) and two analogues of CAPE. Tumor necrosis factor (TNF) activation of NF-κB is completely blocked by CAPE in a dose- and time-dependent manner, as is activation by phorbol ester, ceramide, hydrogen peroxide, and okadaic acid. Additionally, capsaicin (8-methyl-N-vanillyl-6-noneamide) and resiniferatoxin inhibit the activation of NF-κB induced by different agents.

3 Claims, 18 Drawing Sheets

Capsaicin

Resiniferatoxin

Phorbol myristate acetate

INHIBITION OF NUCLEAR TRANSCRIPTION FACTOR NF-κB BY CAFFEIC ACID PHENETHYL ESTER (CAPE), DERIVATIVES OF CAPE, CAPSAICIN (8-METHYL-N-VANILLYL-6-NONENAMIDE) AND RESINIFERATOXIN

CROSS-REFERENCE TO RELATED APPLICATION

This application claims benefit of provisional application U.S. Ser. No. 60/024,602 filed Sep. 5, 1996, now abandoned.

BACKGROUND OF THE INVENTION

1. Field of the Invention

The present invention relates generally to inhibitors of nuclear transcription factor NF-κB, and the use of these inhibitors in the treatment of pathological conditions in humans. Specifically, the present invention relates to the inhibition of nuclear transcription factor NF-κB by Caffeic Acid Phenethyl Ester (CAPE); a 5, 6-dihydroxy, bicyclic derivative of CAPE; a 2, 5-dihydroxy derivative of CAPE; capsaicin (8-methyl-N-vanillyl-6-nonenamide); and resiniferatoxin, and methods for using these inhibitors in the treatment of pathological conditions such as toxic shock, acute inflammatory conditions, acute phase response, atherosclerosis and cancer.

2. Description of the Related Art

Nuclear Factor NF-κB is a protein specific to B cells and binds to a specific DNA sequence within the immunoglobin light chain κ locus enhancer region. Members of the transcription factor NF-κB family have been identified in various organisms, ranging from flies to mammals (see Nolan, et al., Curr. Opin. Genet. Dev. 2:211–20(1992); Liou, et al., Curr. Opin. Genet. Dev. 5:477–87(1993); and Baeuerle and Henkel, Annu. Rev. Immunol. 12:141–79(1994)). Members of this transcription factor family are 35 to 61% homologous to each other and have a Rel homology domain of about 300 amino acids.

In mammals, the most widely distributed κB-binding factor is a heterodimer consisting of p50 and p65 (Rel-A) proteins. This transcription factor plays a central role in various responses, leading to host defense through rapid induction of gene expression. In particular, it controls the expression of various inflammatory cytokines, the major histocompatibility complex genes and adhesion molecules involved in tumor metastasis. Dysregulation of NF-κB and its dependent genes has been associated with various pathological conditions including toxic/septic shock, graft vs. host reaction, acute inflammatory conditions, acute phase response, viral replication, radiation damage, atherosclerosis, and cancer (see Baeuerle and Henkel, Annu. Rev. Immunol. 12:141–79 (1994); and Siebenlist, et al, Annu. Rev. Cell Biol. 10:405–55(1994)).

Unlike other transcription factors, the NF-κB proteins are held in the cytoplasm in an inactive state by an inhibitory subunit called IκBa. The phosphorylation of IκB and its subsequent degradation allows translocation of NF-κB to the nucleus. This activation is induced by many agents, such as inflammatory cytokines (e. g., tumor necrosis factor (TNF), lymphotoxin (LT), and interleukin (IL)-1), mitogens, bacterial products, protein synthesis inhibitors, oxidative stress ($H_2O_2$), ultraviolet light, and phorbol esters. Agents that can downmodulate the activation of NF-κB may be used for therapeutic treatment for these pathological conditions. The present invention is drawn to several such agents.

One agent is caffeic acid (3, 4-dihydroxy cinnamic acid) phenethyl ester (CAPE), a structural relative of flavonoids that is an active component of propolis from honeybee hives. It has antiviral, anti-inflammatory, and immunomodulatory properties, and has been shown to inhibit the growth of different types of transformed cells (see Grunberger, et al., Experientia 44:230–32 (1988); Burke, et al., J. Med. Chem. 38:4171–78(1995); Su, et al., Cancer Res. 54:1865–70 (1994); Su, et al., Mol. Carcinog. 4:231–42 (1991); Hlandon, et al., Arzneim.-Forsch./Drug Res. 30:1847–48 (1980); and Guarini, L., et al., Cell. Mol. Biol. 38:513–27 (1992)). In transformed cells, CAPE alters the redox state and induces apoptosis. Further, it has been reported that CAPE suppresses lipid peroxidation; displays antioxidant activity; and inhibits ornithine decarboxylase, protein tyrosine kinase, and lipoxygenase activities. CAPE can also inhibit phorbol ester-induced $H_2O_2$ production and tumor promotion (see Bhimani, et al. , Cancer Res. 53:4528–33 (1993) and Frenkel, et al., Cancer Res. 53:1255–61 (1993)).

Another such downmodulating agent presented in this disclosure is capsaicin. Capsaicin is a homovanillic acid derivative (8-methyl-N-vanillyl-6-nonenamid) with a molecular weight of 305.42. It is an active component of the red pepper of the genus Capsicum, and has been used in humans for topical treatment of cluster headache, herpes zoster, and vasomotor rhinitis (see Holzer, P., Pharmacol. Rev. 43:143 (1994); Sicuteri, et al., Med. Sci. Res. 16:1079 (1988); Watson, et al., Pain 33:333 (1988); Marabini, et al., Regul. Pept. 22:1 (1988)). In vitro capsaicin modulates cellular growth, collagenase synthesis, and prostaglandin secretion from rheumatoid arthritis synoviocytes (see Matucci-Cerinic, et al., Ann. Rheum. Dis. 49:598 (1990)). Capsaicin has also been shown to be simmunomodulatory as indicated by its ability to modulate lymphocyte proliferation, antibody production, and neutrophil chemotaxis (see Nilsson, et al., J. Immunopharmac. 10:747 (1988); Nilsson, et al., J Immunopharmac. 13:21 (1991); and Eglezos, et al, J Neuroimmunol. 26:131 (1990)). These effects play an important role in capsaicin's use for treatment of arthritis. In addition, capsaicin induces mitochondrial swelling, inhibits NADH oxidase, induces apoptosis of transformed cells, stimulates adenylate cyclase, activates protein kinase C, inhibits superoxide anion generation and alters the redox state of the cell.

Various effects of capsaicin are mediated through a specific cellular receptor referred to as vanilloid receptor that is shared by resiniferatoxin. Like capsaicin, resiniferatoxin is an alkaloid derived from plants of the genus Euphorbia. Resiniferatoxin is a structural homologue of capsaicin (see FIG. 1). Resiniferatoxin is also structurally similar to phorbol esters (phorbol myristate acetate), which interacts with distinct binding sites and activates protein kinase C (see Szallasi, et al., Neurosci. 30:515 (1989); and Szallasi and Blumberg, Neurosci. 30:515 (1989)). Unlike resiniferatoxin, capsaicin has no homology to phorbol myristate acetate, but like resiniferatoxin, it too activates protein kinase C, suggesting that the latter activation is not due to the phorbol ester-like moiety on resiniferatoxin. Resiniferatoxin has been shown to mimic many of the actions of capsaicin.

Thus, inhibition of nuclear transcription factor NF-κB by Caffeic Acid Phenethyl Ester (CAPE); a 2,5-hydroxy derivative of CAPE; a 5, 6-dihydroxy, bicyclic derivative of CAPE, Capsaicin (8-methyl-N-vanillyl-6-nonenamide), and Resiniferatoxin is unknown in the prior art. The inhibition of NF-κB is an important step in the treatment of various pathological conditions which result from the activation of NF-κB by inflammatory cytokines, mitogens, oxidative stress, phorbol esters and other agents. The present invention fulfills a long-standing need and desire in the art to treat such pathological conditions.

SUMMARY OF THE INVENTION

One object of the present invention is to provide methods of inhibition of the activation of NF-κB using various inhibitory agents.

In an embodiment of the present invention, there is provided the inhibitory agent Caffeic Acid Phenethyl Ester (CAPE).

In an additional embodiment of the present invention, there is provided as an inhibitor of NF-κB, a 2,5-dihydroxy derivative of Caffeic Acid Phenethyl Ester (CAPE).

In yet another embodiment of the present invention, there is provided as an inhibitor of NF-κB, a bicyclic, 5, 6-dihydroxy derivative of Caffeic Acid Phenethyl Ester (CAPE).

In an additional embodiment of the present invention, there is provided the inhibitory agent Capsaicin (8-methyl-N-vanillyl-6-nonenamide).

In yet another embodiment of the present invention, resiniferatoxin is provided as an inhibitor of NF-κB.

An additional object of the present invention is to provide methods for treating a pathological condition caused by the activation of NF-κB in an individual, comprising the step of administering caffeic acid phenethyl ester (CAPE), a 5, 6-bicyclic dihydroxy derivative of CAPE, a 2, 5-dihydroxy derivative of CAPE, capsaicin (8-methyl-N-vanillyl-6-nonenamide), or resiniferatoxin to an individual to be treated.

Various embodiments of this aspect of the invention include providing methods for treating a pathological condition such as toxic/septic shock, graft vs. host reaction, acute inflammatory conditions, acute phase response, viral infection, radiation damage susceptibility, atherosclerosis, and cancer, comprising the step of administering caffeic acid phenethyl ester (CAPE); a 2, 5-dihydroxy derivative of CAPE; a bicyclic 5, 6-dihydroxy derivative of CAPE; capsaicin (8-methyl-N-vanillyl-6-nonenamide); or resiniferatoxin to an individual to be treated.

Other and further aspects, features, and advantages of the present invention will be apparent from the following description of the presently preferred embodiments of the invention. These embodiments are given for the purpose of disclosure.

1B upper panel: For supershift and specificity analysis of NF-κB activation, nuclear extracts were prepared from untreated or TNF (0.1 nM)-treated cells, incubated for 30 minutes with antibodies, then assayed for NF-κB.

1B lower panel: Cells were preincubated at 37° C. with 25 μg/ml CAPE for different times and then tested for NF-κB activation at 37° C. for 15 minutes either with or without 0.1 nM TNF. (−) indicates CAPE was present before the addition of TNF, (0) indicates co-incubation with TNF, and (+) indicates CAPE was added after TNF. After these treatments, nuclear extracts were prepared and assayed for NF-κB. The arbitrary units represent the relative amounts of radioactivity present in respective bands.

Figure 1A:
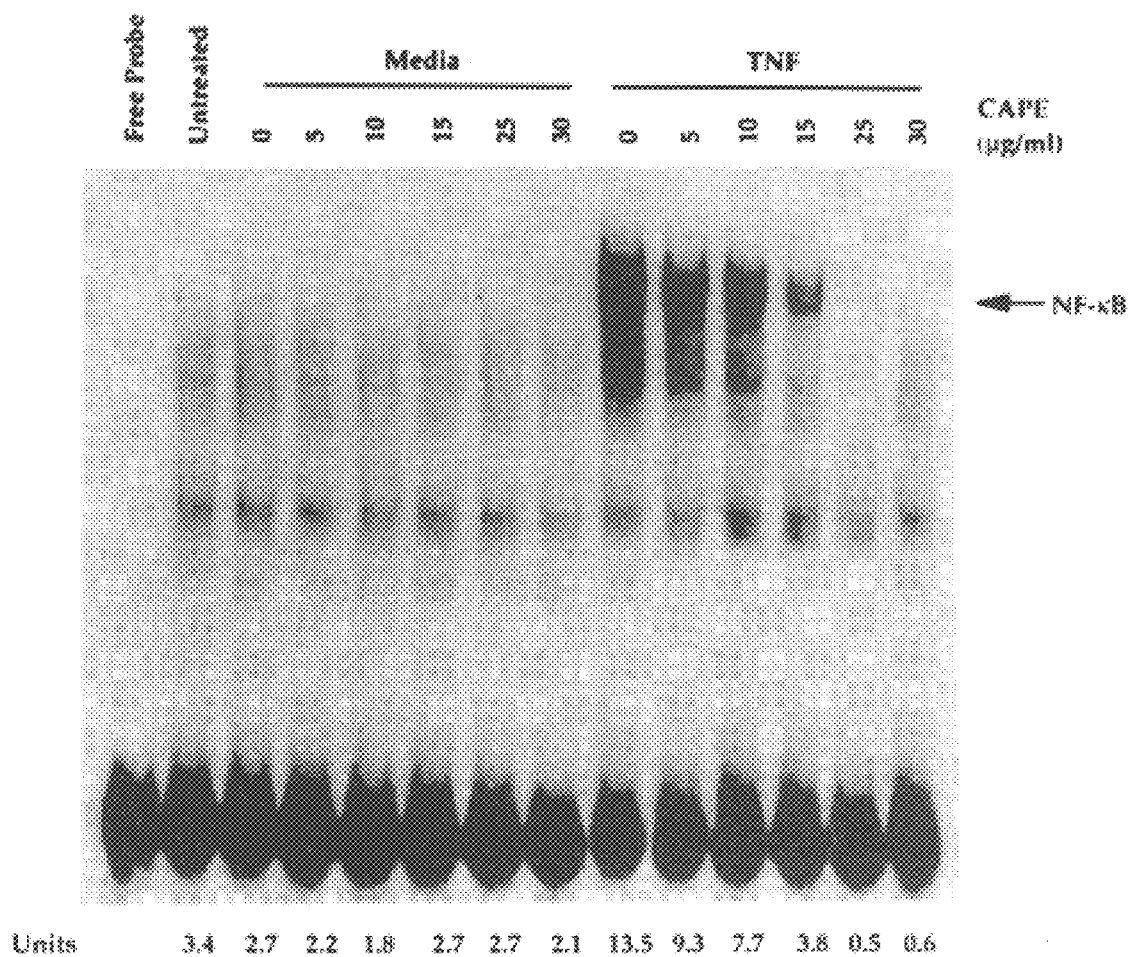
FIG. 1. Dose response and kinetics of inhibition of TNF-dependent NF-κB by CAPE is shown. 1A: U937 cells ($2\times10^6$/ml) were preincubated at 37° C. for 2 hours with the indicated concentrations of CAPE followed by a 15- minute incubation with 0.1nM TNF.
Figures 1, 1B:
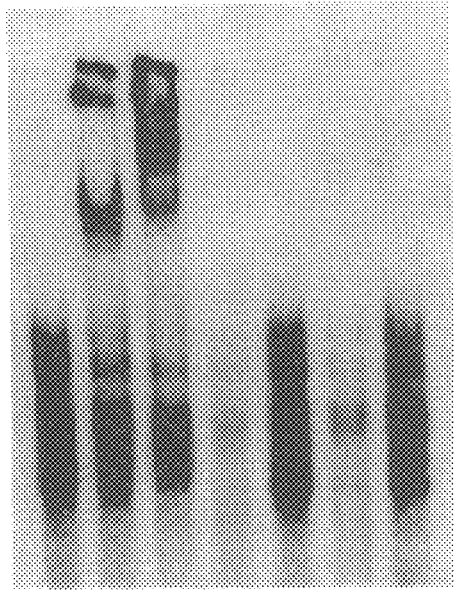
Figures 1, 1B, 2:
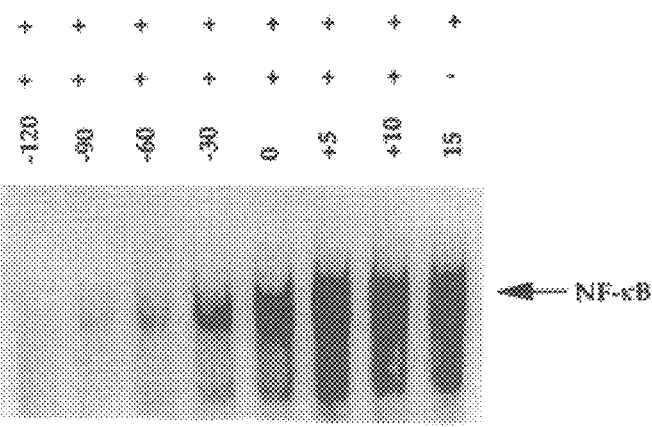

FIG. 2: Demonstrated is the effect of CAPE on phorbol myristate acetate-, ceramide-, okadaic acid- and $H_2O_2$- mediated activation of NF-κB. U937 cells ($2\times10^6$/ml) were preincubated for 120 minutes at 37° C. with CAPE (25 μg/ml) followed by treatments at 37° C. with either phorbol myristate acetate (100 ng/ml for 60 minutes); or $H_2O_2$ (0.5 mM for 30 minutes) or ceramide-C8 (10 μM for 30 minutes) or okadaic acid (500 nM for 30 minutes) and then tested for NF-κB activation. The electrophoretic mobility shift assay run for phorbol myristate acetate mediated activation was separate from the others.

FIG. 3: Shown is the effect of CAPE on the binding of NF-κB to DNA. For 3A, nuclear extracts prepared from TNF activated U937 cells were incubated at 37° C. with indicated concentrations of CAPE for 30 minutes, then analyzed for NF-κB activation. For 3B, cytoplasmic extracts from untreated cells were treated with deoxycholate in the presence or absence of indicated concentrations of CAPE and analyzed for NF-κB activation.

Figure 4:
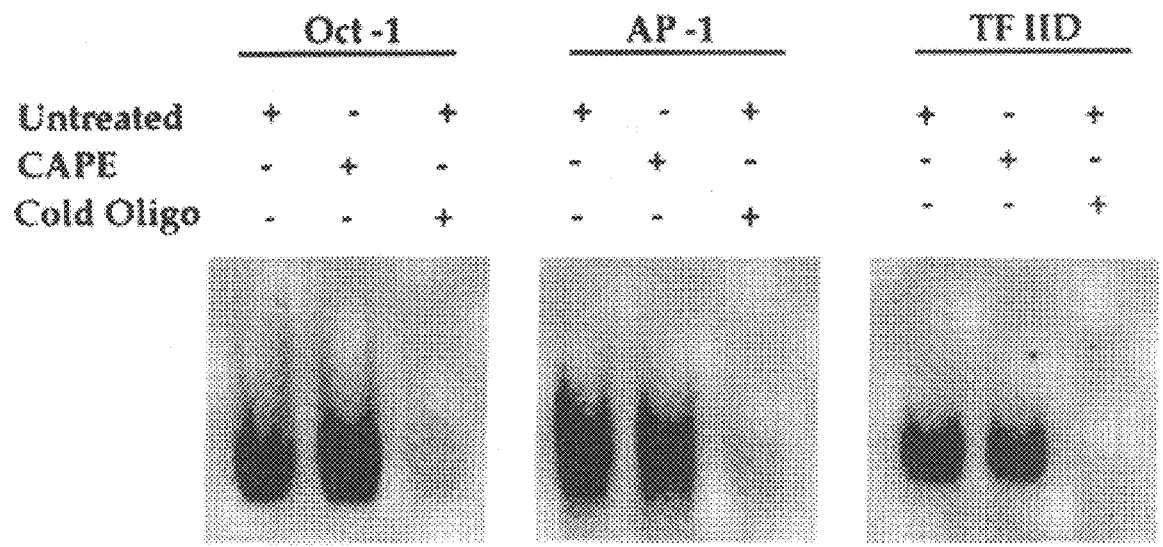

FIG. 4: Shown is the effect of CAPE on AP-1, Oct-1 and TFII D transcription factors. Cells were treated with 25 μg/ml of CAPE for 2 hours at 37° C., and nuclear extracts were prepared and used for the electrophoretic mobility shift assays.

FIG. 5: The effect of CAPE on TNF-induced degradation of IκBa and on the level of p65 in the cytoplasm and nucleus is shown. U937 cells ($2\times10^6$/ml) pretreated for 2 hours at 37° C. with or without CAPE (25 μg/ml) were incubated for different times with and without TNF (0.1 nM), then assayed for IκBa (upper panel). For p65 (lower panel), cells pretreated for 2 hours at 37° C. with or without CAPE (25 μg/ml) were incubated for 15 minutes with and without TNF (0.1 nM), and nuclear and cytoplasmic extracts were prepared and assayed for p65 by western blot analysis.

Figure 6:
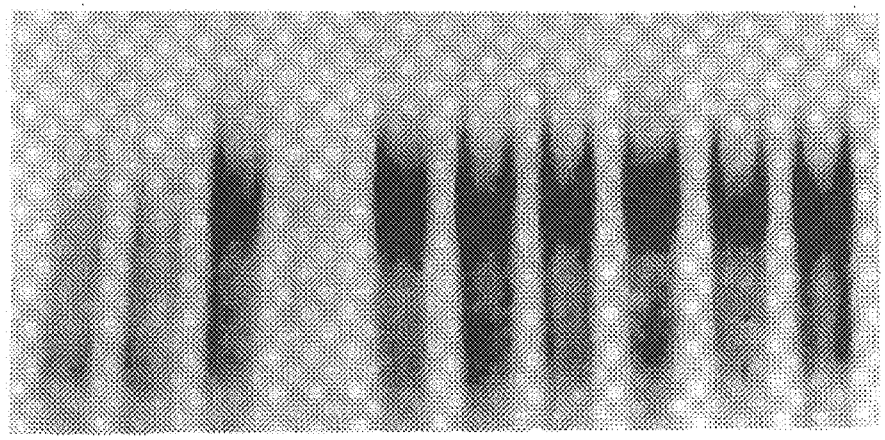

FIG. 6: The effect of DTT, BME and DMP on the CAPE-induced inhibition of NF-κB activation is shown. U-937 cells ($2\times10^6$/ml) were incubated for 2 hours with DTT (100 μM), BME (142 μM) or DMP (100 μM) in the presence or absence of CAPE (25 μg/ml), activated with TNF (0.1 nM) for 15 minutes, then assayed for NF-κB activation.

Figure 7A:
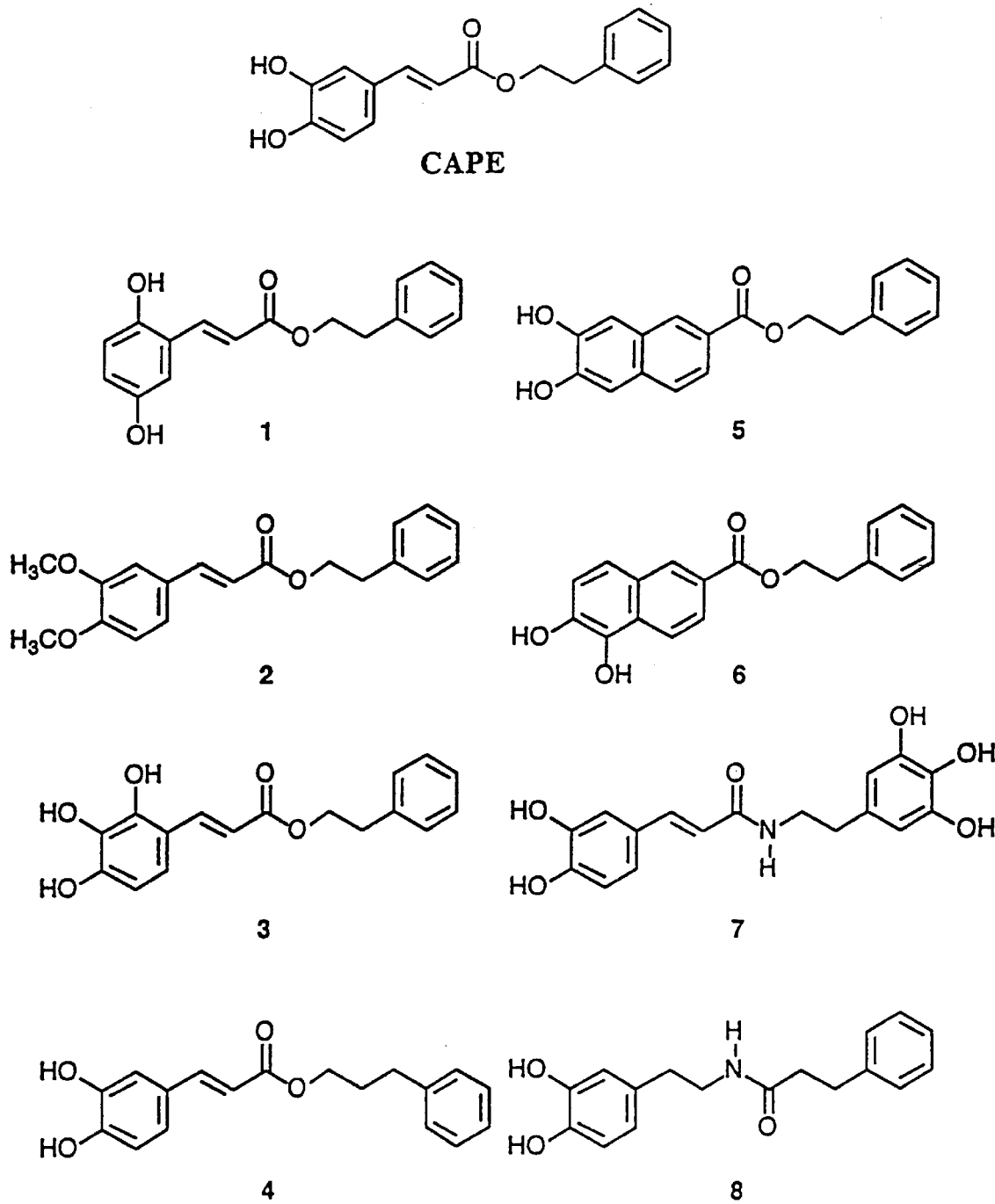
Figures 1, 7B:
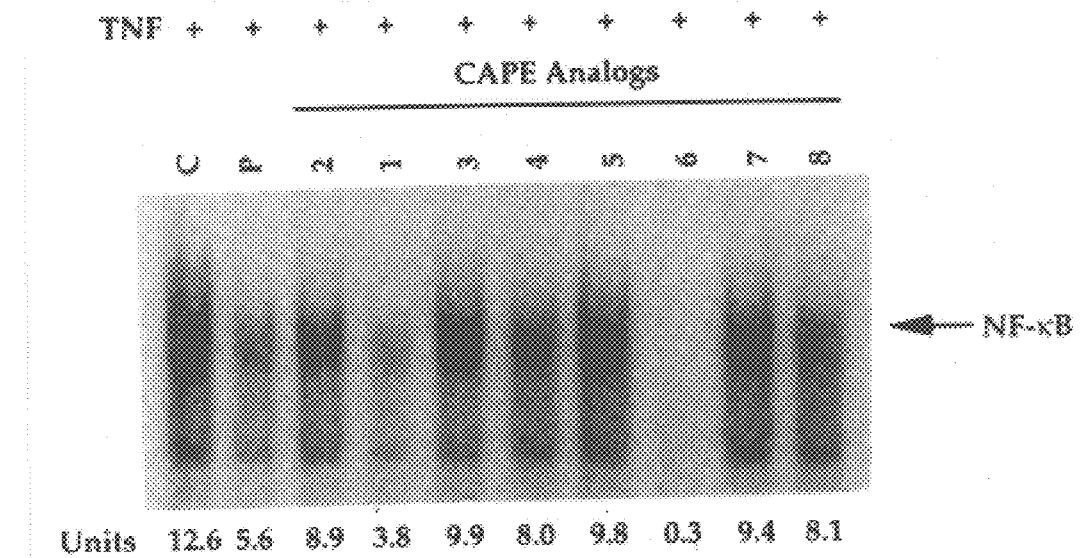
Figures 2, 7B:
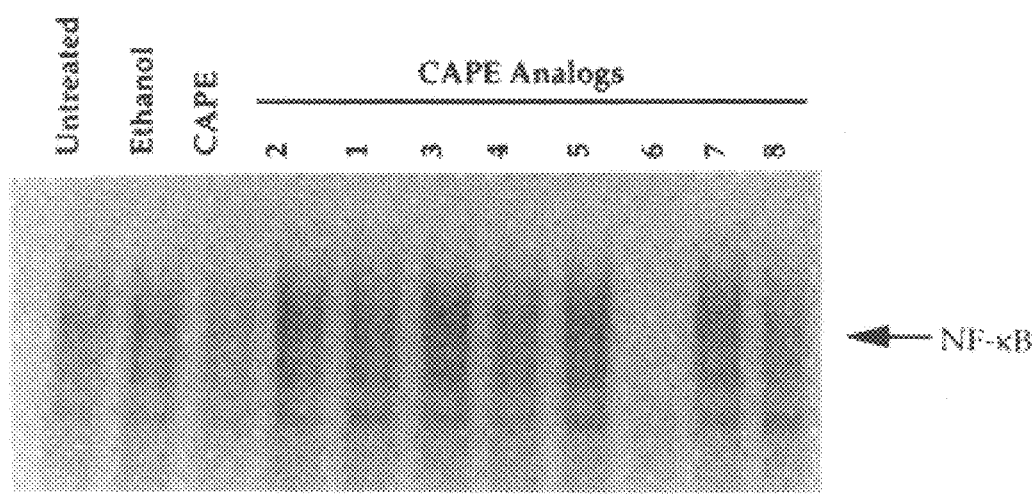

FIG. 7: Shown are the structures of different analogues of CAPE (7A) and their effect on TNF-induced NF-κB activation (7B). U-937 cells ($2\times10^6$/ml) were incubated for 2 hours with different analogues of CAPE (25 μg/ml) at 37° C. , activated either with (upper panel) or without (lower panel) TNF (0.1 nM) for 15 minutes, and assayed for NF-κB activation. C denotes TNF treatment only and P denotes treatment with parent compound CAPE followed by TNF. The arbitrary units represent the relative amounts of the radioactivity present.

Figure 8A:
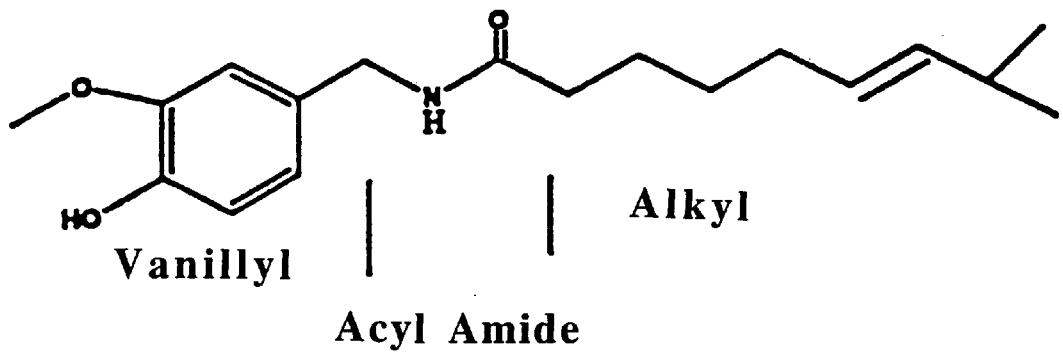

FIG. 8: Shown is the homology in the chemical structure of capsaicin, resiniferatoxin and phorbol myristate acetate.

FIG. 9: Shown are the reseutls of electrophoretic mobility shift assays demonstrating the dose response and kinetics of capsaicin for the inhibition of TNF-dependent NF-κB.

9A: ML-1a cells ($2\times10^6$/ml) were preincubated at 37° C. for 2 hours with different concentrations of capsaicin and then for 15 minutes with or without 0.1 nM TNF.

9B: Cells ($2\times10^6$/ml) were preincubated at 37° C. for 2 hours with 300 μM capsaicin and then tested for NF-κB activation at 37° C. for 15 minutes with different concentrations of TNF as indicated.

9C: ML-1a cells ($2\times10^6$/ml) were preincubated at 37° C. with 300 µM capsaicin for different times and then tested for NF-κB activation at 37° C. for 15 minutes with 0.1 nM TNF. (−) indicates time capsaicin was present before the addition of TNF, (0) indicates co-incubation with TNF, and (+) indicates time capsaicin was added after TNF. After these treatments, nuclear extracts were prepared and assayed for NF-κB.

Figure 10:
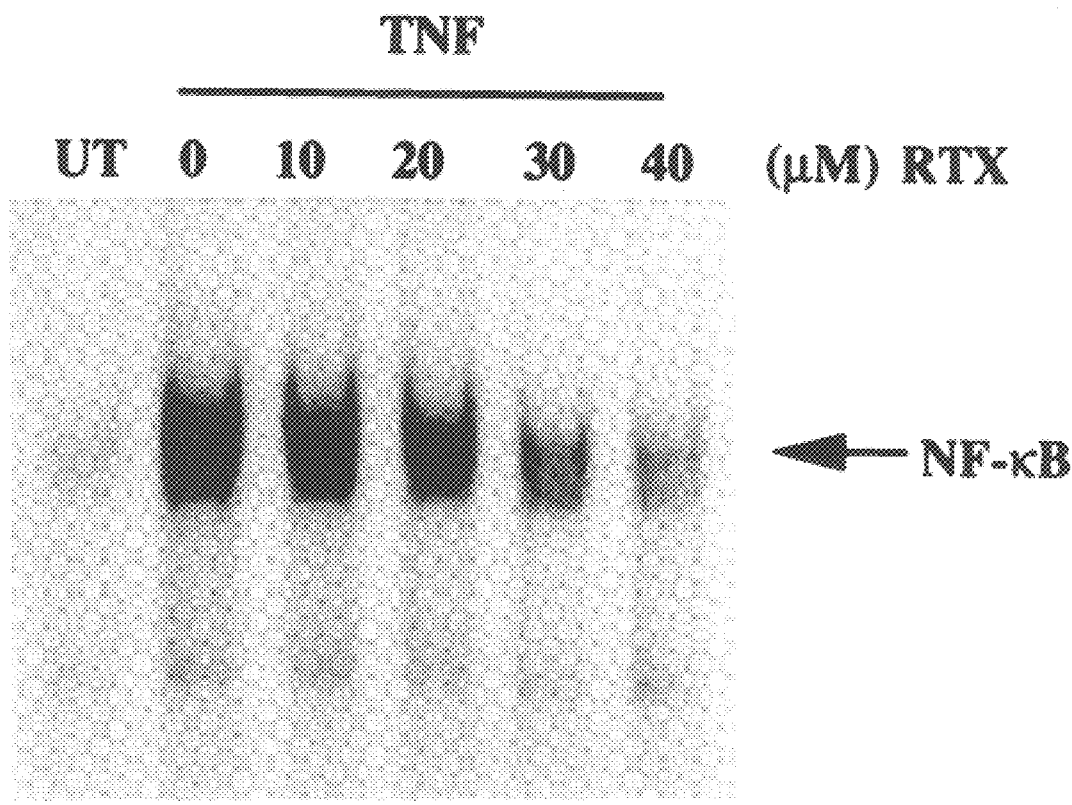

FIG. 10: Shown is the dose response of inhibition of TNF-dependent NF-κB activation by resiniferatoxin. Cells ($2\times10^6$/ml) were preincubated at 37° C. for 2 hours with different concentrations of resiniferatoxin as indicated, activated at 37° C. for 30 minutes with 0.1 nM of TNF, then tested for NF-κB. After these treatments, nuclear extracts were prepared and then assayed for NF-κB. UT stands for untreated cells.

FIG. 11: Super-shift assay and specificity of the effect of capsaicin on the NF-kB activation. For panel (A), nuclear extracts were prepared from untreated or TNF-treated (0.1 nM) cells ($2\times10^6$/ml), incubated for 30 minutes with antibodies and then assayed for NF-κB. For panel (B), cells were treated with different concentrations of capsaicin for 2 hours and with TNF for 15 minutes, cytoplasmic extracts were prepared, and these extracts were treated with 8% deoxycholate and assayed for NF-κB by electrophoretic mobility shift assay. For panel (C), nuclear extracts from TNF-treated cells were incubated with different concentrations of capsaicin for 15 minutes and analyzed for NF-κB by electrophoretic mobility shift assay.

FIG. 12: Shown is the effect of capsaicin on different activators (phorbol myristate acetate and okadaic acid) of NF-κB. For panel 12A, ML-1a cells ($2\times10^6$/ml) were preincubated for 2 hours at 37° C. with capsaicin, treated with either phorbol myristate acetate (25 ng/ml) or okadaic acid (500 nM) or TNF (0.1 nM) for 30 minutes, and then tested for NF-κKB activation. 100-fold excess of cold or mutated oligonucleotide was used to determine the specificity of binding. For the lane labeled as Mut. probe, mutated probe was labeled and then used to test the binding.

For panel 12B, U-937 or Hela cells ($2\times10^6$/ml) were preincubated for 2 hours at 37° C. with indicated concentration of capsaicin followed by TNF (0.1 nM) for 15 minutes, and then tested for NF-kB.

FIG. 13: The effect of capsaicin on TNF-induced degradation of IκBa and on the level of p65 is shown.

13A: ML-1a ($2\times10^6$/ml) cells either untreated or pretreated for 2 hours with 300 uM capsaicin at 37° C. were incubated for different times with TNF (0.1 nM), then assayed for IκBa in cytosolic fractions by western blot analysis. S and N represent slow- and normal-migratory bands.

13B: Cells were treated with capsaicin for different time periods then assayed for either IκBa or p65 in cytosolic fraction by western blot analysis.

13C: ML-1a ($2\times10^6$/ml) cells pretreated for 2 hours with capsaicin were incubated with TNF (0.1 nM) for 30 minutes, then nuclear and cytoplasmic extracts were assayed for p65 by Western blot analysis.

13D: Cells were pretreated with different concentrations of capsaicin for 2 hours followed by treatment with or without TNF (0.1 nM) for 15 minutes, then cytosolic fractions were assayed for either p50 or c-Rel by western blot analysis.

Figure 14:
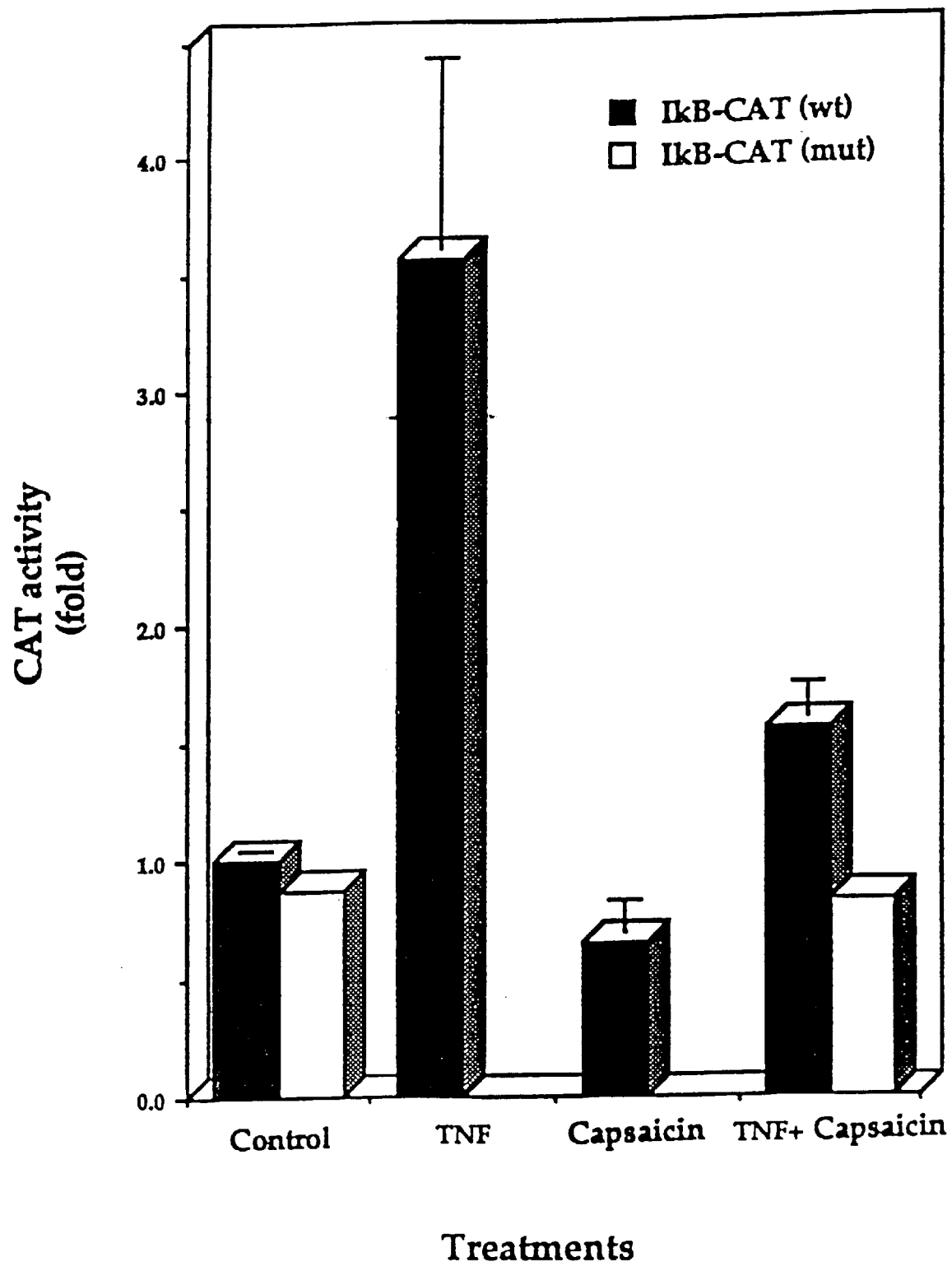

FIG. 14: Shown is the effect of capsaicin on the acitivity of IκBa promoter linked to the CAT gene. Cells were transiently transfected with pIκBCAT and pmutIκBCAT, treated with 300 µM capsaicin for 2 hours, exposed to 0.1 nM TNF for 1 hour, and assayed for CAT activity. Results are expressed as fold activity over the untreated control.

The appended drawings have been included herein so that the above-recited features, advantages and objects of the invention will become clear and can be understood in detail. These drawings form a part of the specification. It is to be noted, however, that the appended drawings illustrate preferred embodiments of the invention and should not be considered to limit the scope of the invention.

DETAILED DESCRIPTION OF THE INVENTION

It will be apparent to one skilled in the art that various substitutions and modifications may be made to the invention disclosed herein without departing from the scope and spirit of said invention.

As used herein, the term "nuclear factor NF-κB" or "NF-κB" shall refer to the protein specific to B cells that binds to a specific DNA sequence (5-GGGGACTTTCC-3) within the immunoglobin light chain κ locus enhancer region, and in mammals is a heterodimer consisting of p50 and p65 (Rel-A) proteins. NF-κB plays a central role in various responses, leading to host defense through rapid induction of gene expression, and controls the expression of various inflammatory cytokines, the major histocompatibility complex genes, and adhesion molecules involved in tumor metastasis.

As used herein, the term "CAPE" shall refer to caffeic acid (3, 4-dihydroxy cinnamic acid) phenethyl ester.

As used herein, the term "5, 6- dihydroxy, bicyclic derivative of CAPE" shall refer to the CAPE analogue molecule presented at FIG. 7A compound no. 6.

As used herein the term "2, 5-dihydroxy derivative of CAPE" shall refer to the CAPE analogue molecule presented at FIG. 7A compound no. 1.

As used herein, the term "capsaicin" shall refer to a homovanillic acid derivative, 8-methyl-N-vanillyl-6-nonenamid, with a molecular weight of 305.42.

Figure 8B:
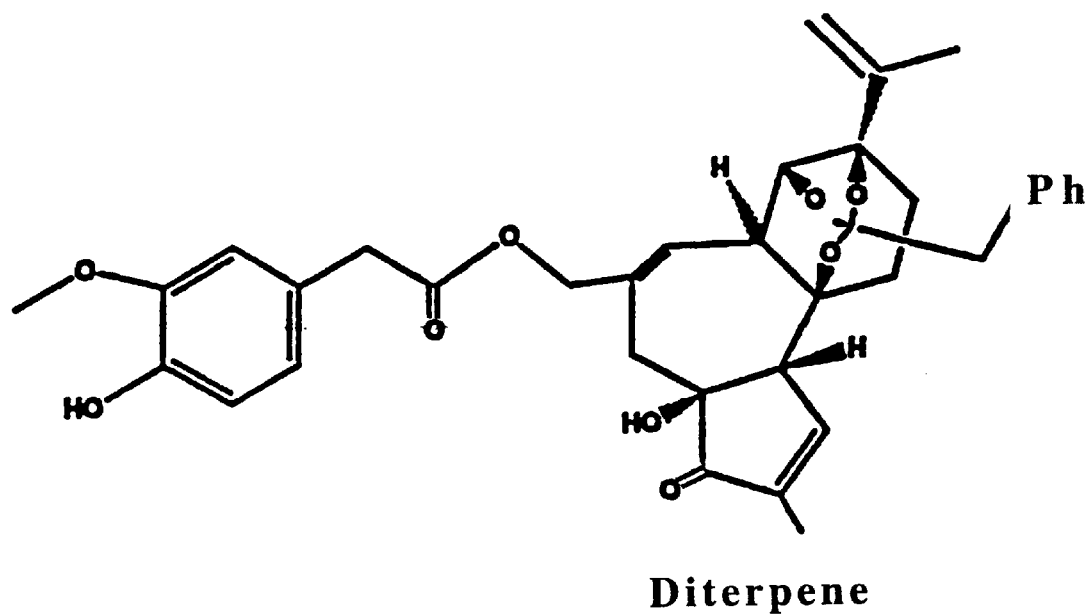
Figure 8C:
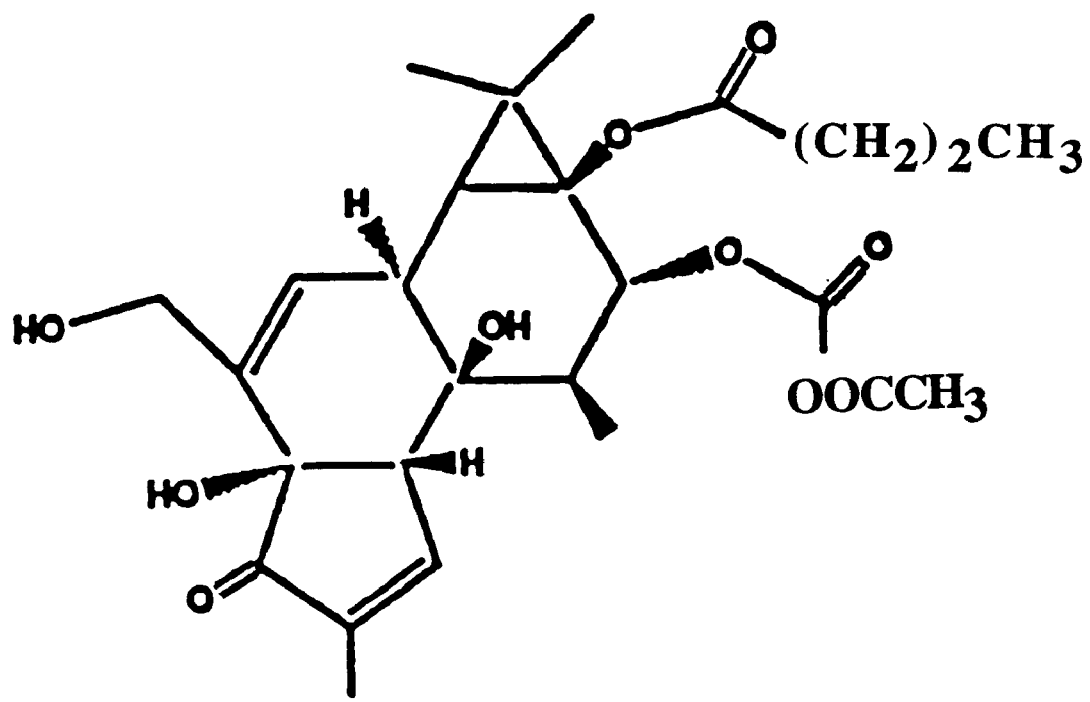

As used herein, the term "resiniferatoxin" shall refer to the structural homologue of capsaicin shown in FIG. 8B.

As used herein, the term "pathological condition" shall refer to conditions that relate to or are caused by disease. Such conditions may include, but are not limited to, toxic or septic shock, graft vs. host reaction, acute inflammatory conditions, acute phase response, viral replication, radiation damage, atherosclerosis, and cancer.

As used herein, the term "therapeutically effective amount" of an agent shall refer to an amount of that agent which is physiologically significant and imaproves an individual's health. An agent is "physiologically significant" if its presence results in a change in the physiology of the recipient human. For example, in the treatment of a pathological condition, administration of an agent which relieves or arrests further progress of the condition would be considered both physiologically significant and therapeutically effective.

As used herein, the term "CAT" shall refer to chloramphenicol acetyltransferase.

The present invention is directed to methods of inhibition of the activation of NF-κB using various inhibitory agents. It is contemplated additionally that methods for treating a pathological condition in an individual caused by the activation of NF-κB are presented.

For the therapeutic applications, a person having ordinary skill in the art of molecular pharmacology would be able to determine, without undue experimentation, the appropriate dosages and routes of administration of the novel inhibitors of the activation of NF-κB of the present invention.

The following examples are given for the purpose of illustrating various embodiments of the invention and are not meant to limit the present invention in any fashion:

EXAMPLE 1

Materials

Penicillin, streptomycin, RPMI 1640 medium, and fetal calf serum were obtained from GIBCO (Grand Island, N.Y.). Phorbol ester and bovine serum albuminutes were obtained from Sigma Chemical Co. (St. Louis, Mo.). Bacteria-derived recombinant human TNF, purified to homogeneity with a specific activity of $5 \times 10^7$ units/mg, was kindly provided by Genentech, Inc. (South San Francisco, Calif.). Antibody against IκBa, cyclin D1, and the NF-κB subunits p50 and p65 and double-stranded oligonucleotides having AP-1 and Oct-1 consensus sequences were obtained from Santa Cruz Biotechnology (Santa Cruz, Calif.). Ceramide (C8) was obtained from Calbiochem (San Diego, Calif.). Tris, glycine, NaCl, SDS, resiniferatoxin, phorbol myristate acetate, chloramphenicol, and bovine serum albumin were obtained from Sigma Chemical Co. (St. Louis, Mo.). $^{32}$P-labeled γ-ATP with a specific activity of 7000 Ci per mmole was obtained from ICN (Costa Mesa, Calif.). Okadaic acid (OA) was obtained from LC Laboratories (Woburn, Mass.), capsaicin from Tocris Cookson Inc. (St. Louis, Mo.), acetyl coenzyme A from Pharmacia Biotech (Alameda, Calif.), and tritiated acetyl coenzyme A from Amersham Life Sciences (Arlington Heights, Ill.). The GIBCO-BRL calcium phosphate transfection system-kit (Cat. #18306-019) was obtained from Life Technologies (Madison, Wis.).

CAPE and its Analogue

For structure-activity relationship studies, several analogues of CAPE were synthesized as described by Grunberger, et al., *Experientia* 44:230–32 (1988) and Burke, et al, *J. Med. Chem.* 38:4171–78 (1995). These analogues included ring substituents, ester groups, rotationally constrained variants and saturated amide analogues. Stock solutions of CAPE and its analogues were made in 50% ethanol at 1–5 mg/ml and further dilutions were made in cell culture medium.

Cell Lines

For the CAPE studies, the human histiocytic cell line U937 cells were grown routinely in RPMI 1640 medium supplemented with glutamine (2 mM), gentamicin (50 mg/ml), and fetal bovine serum (FBS) (10%). The cells were seeded at a density of $1 \times 10^5$ cells/ml in T25 flasks (Falcon 3013, Becton Dickinson Labware, Lincoln Park, N.J.) containing 10 ml of medium and grown at 37° C. in an atmosphere of 95% air and 5% $CO_2$. Cell cultures were split every 3 or 4 days. Occasionally, cells were tested for mycoplasma contamination using the DNA-based assay kit purchased from Gen-Probe (San Diego, Calif.).

Studies with capsaicin and resiniferatoxin were performed with ML-1a, a human myelomonoblastic leukemia cell line kindly provided by Dr. Ken Takeda (Showa University, Japan); and U937 and HeLa cell lines, which were obtained from ATCC. The cells were grown routinely in RPMI 1640 medium supplemented with glutamine (2 mM), gentamicin (50 mg/ml), and fetal bovine serum (FBS) (10%). The cells were seeded at a density of $1 \times 10^5$ cells/ml in T25 flasks (Falcon 3013, Becton Dickinson Labware, Lincoln Park, N.J.) containing 10 ml of medium and grown at 37° C. in an atmosphere of 95% air and 5% $CO_2$. Cell cultures were split every 3 or 4 days.

DNA Constructs

IκBa plasmid, pIκBCAT containing a 0.2 kb upstream fragment linked to the chloramphenicol acetyltransferase (CAT) gene, and a plasmid pmutIκBCAT also containing the 0.2 kb fragment but with a mutated NF-κB site linked to CAT, were kindly supplied by Dr. Paul Chiao of the M. D. Anderson Cancer Center, Houston, Tex. The characterization of these plasmids has been described in detail in Schreiber, et al., *Nucleic Acids Res.* 17:6419 (1989).

EXAMPLE 2

Electrophoretic Mobility Shift Assays

These assays were carried out as described in detail previously by Chaturvedi, et al., *J. Biol. Chem.* 269:14575–83 (1994); and Schreiber, et al., *Nucleic Acids Res.* 17:6419 (1989). Briefly, $2 \times 10^6$ cells were washed with cold phosphate-buffered saline (PBS) and suspended in 0.4 ml of lysis buffer (10 mM HEPES pH 7.9, 10 mM KCl, 0.1 mM EDTA, 0.1 mM EGTA, 1 mM DTT, 0.5 mM PMSF, 2.0 mg/ml leupeptin, 2.0 mg/ml aprotinin, and 0.5 mg/ml benzamidine). The cells were allowed to swell on ice for 15 minutes, after which 12.5 ml of 10% NP-40 was added. The tube was then vortexed vigorously for 10 seconds, and the homogenate was centrifuged for 30 seconds. The nuclear pellet was resuspended in 25 μl ice-cold nuclear extraction buffer (20 mM HEPES pH 7.9, 0.4 M NaCl, 1 mM EDTA, 1 mM EGTA, 1 mM DTT, 1 mM PMSF, 2.0 mg/ml leupeptin, 2.0 mg/ml aprotinin, and 0.5 mg/ml benzamidine), and incubated on ice for 30 minutes with intermittent mixing. Samples were centrifuged for 5 minutes at 4° C., and the supernatant (nuclear extract) was either used immediately or stored at −70° C. The protein content was measured by the method of Bradford, M. M., *Anal. Biochem.* 72:248–254 (1976).

Electrophoretic mobility shift assays were performed by incubating 4 mg of nuclear extract with 16 fmoles of $^{32}$P end-labeled, 45-mer double-stranded NF-κB oligonucleotide from the HIV-LTR:

(Nabel, G. and Baltimore, D., *Nature* 326:711–13 (1987)) for 15 minutes at 37° C. The incubation mixture included 2–3 mg of poly-(dI-dC) in a binding buffer (25 mM HEPES pH 7.9, 0.5 mM EDTA, 0.5 mM DTT, 1% NP-40, 5% glycerol, and 50 mM NaCl). The DNA-protein complex formed was separated from free oligonucleotide on a 4.5% native polyacrylamide gel using buffer containing 50 mM Tris, 200 mM glycine pH 8.5, and 1 mM EDTA, and the gel then was dried. A double-stranded mutated oligonucleotide:

was used to examine the specificity of binding of NF-κB to the DNA. The specificity of binding was also examined by competition with the unlabeled oligonucleotide.

For supershift assays, nuclear extracts prepared from TNF-treated cells were incubated with the antibodies against either p50 or p65 subunits of NF-κB for 30 minutes at room temperature before the complex was analyzed by electrophoretic mobility shift assay (Singh, S. and Aggarwal, B. B, *J. Biol. Chem.* 270:10631–39 (1995)). Antibody against cyclin D1 was included as a negative control.

The electrophoretic mobility shift assays for AP-1, TFII D and Oct-1 were performed as described for NF-κB, using $^{32}$P end-labeled double-stranded oligonucleotides. Specificity of binding was determined routinely by using an excess of unlabeled oligonucleotide for competition as described by Singh, S. and Aggarwal, B. B, *J. Biol. Chem.* 270:10631–39 (1995). Visualization and quantitation of radioactive bands was carried out by phosphorimager (Molecular Dynamics, Sunnyvale, Calif.) using 'Image-quant' software.

EXAMPLE 3

Western Blotting for IκBa and p65

After the NF-kB activation reaction, postnuclear extracts were resolved on 10% SDS-polyacrylamide gels for IκBa. To determine p65 levels, nuclear and postnuclear (cytoplasmic) extracts were resolved on 8% SDS-polyacrylamide gels. Proteins were then electrotransferred to Immobilon P membranes, probed with a rabbit polyclonal antibody against IκBa or against p65, and detected by chemiluminescence (ECL-Amersham; 30).

EXAMPLE 4

Effect of CAPE on the Activation of the Transcription Factor NF-kB

U937 cells were used for these studies since the response of U937 cells to NF-κB activation by various stimuli has been well characterized (see Reddy, et al., *J. Biol. Chem.* 269:25369–72 (1994)). Cell viability of greater than 98% was obtained with all concentrations of CAPE and its analogues in these experiments. U937 cells were preincubated for 2 hours with different concentrations of CAPE, treated with TNF (0.1 nM) for 15 minutes at 37° C., then examined for NF-κB activation. Results (FIG. 1A) indicate that CAPE inhibited the TNF-dependent activation of NF-κB in a dose-dependent manner, with the maximum effect occuring at 25 μg/ml. No activation of NF-κB was noted in untreated cells or those treated with either the vehicle (ethanol) alone or with CAPE alone.

To show that the retarded band observed by electrophoretic mobility shift assay in TNF-treated cells was indeed NF-κB, nuclear extracts were incubated with antibodies to either p50 (NF-κB1) or p65 (Rel A) subunits in separate treatments followed by electrophoretic mobility shift assay. The results from this experiment (FIG. 1B, upper panel) show that antibodies to either subunit of NF-κB shifted the band to higher molecular weight, suggesting that the TNF-activated complex consisted of p50 and p65 subunits. Nonspecific antibody against cyclin D had no effect on the mobility of NF-κB. In addition, the retarded band observed by electrophoretic mobility shift assay in TNF-treated cells disappeared when unlabeled oligonucleotide (100-fold in excess) was used but not when the mutated oligonucleotide was used (FIG. 1B, upper panel).

The kinetics of inhibition was examined by incubating the cells with CAPE for 120, 90, 60, and 30 minutes before the addition of TNF, simultaneously with the addition of TNF, and 5 and 10 minutes after the addition of TNF. The cells were treated with TNF for 15 minutes. TNF response was inhibited only when the cells were pretreated with CAPE (FIG. 1B, lower panel). Cotreatment of cells with TNF and CAPE was not effective.

EXAMPLE 5

CAPE also Blocks NF-κB Activation Induced by Phorbol Ester, Ceramide, Okadaic Acid and Hydrogen Peroxide NF-κB activation is also induced by phorbol ester (phorbol myristate acetate), ceramide, okadaic acid and hydrogen peroxide (Meyer, et al., *EMBO J.* 12:2005–15 (1993)). However, the initial signal transduction pathways leading to the NF-κB activation induced b y these agents differ. The effect of CAPE on the activation of the transcription factor by these various agents was therefore examiner. The results shown in FIG. 2 indicate that CAPE completely blocked the activation of NF-κB induced by all four agents. These results suggest that CAPE acts at a step where all these agents converge in the signal transduction pathway leading to NF-κB activation.

EXAMPLE 6

CAPE Inhibits DNA Binding of NF-κB Specifically and not Other Transcription Factors Both TPCK, a serine protease inhibitor, and herbimycin A, a protein tyrosine kinase inhibitor, have been shown to block the activation of NF-κB by their interference with the binding of NF-κB to DNA (Finco, et al., *Proc. Natl. Acad. Sci. U.S.A.* 91:11884–88 (1994); and Mahon, T. M. and O'Neill, L. A. J., *J. Biol. Chem.* 270:28577–64 (1995)). To determine the effect of CAPE on the binding of NF-κB to DNA, the nuclear extracts from TNF-preactivated cells were incubated with various concentrations of CAPE. Electrophoretic mobility shift assays (FIG. 3, upper panel) showed that CAPE prevented NF-κB from binding to DNA. Since IκBa can also be dissociated from NF-κB by a mild treatment with detergent such as deoxycholate, the ability of deoxycholate-treated cytoplasmic extracts to bind to the DNA with or without CAPE treatment was examined. Here, too, CAPE interfered with the binding of NF-κB proteins to DNA (FIG. 3, lower panel).

The ability of CAPE to inhibit the binding of other transcription factors such as AP-1, TFII D and Oct-1 was tested. The effect of CAPE on NF-κB binding was specific, as it did not inhibit the DNA-binding ability of the other transcription factors (FIG. 4)

EXAMPLE 7

CAPE Does Not Inhibit TNF-dependent Phosphorylation and Degradation of IκBa

The translocation of NF-κB to the nucleus is preceded by the phosphorylation and proteolytic degradation of IκBa (see Thanos, D. and Maniatis, T., *Cell* 80:529–32 (1995)). To determine whether the inhibitory action of CAPE was due to an effect on IκBa degradation, the cytoplasmic levels of IκBa protein were examined by western blot analysis. As shown in FIG. 5 upper panel, treatment of cells with CAPE had no effect on the cytoplasmic pool of IκBa, but treatment of cells with TNF decreased the IκBa band within 5 minutes and completely eliminated it in 15 minutes; the band then reappeared by 30 minutes. The presence of CAPE did not affect significantly the TNF-induced rate of degradation of IκBa but it did delay its resynthesis. This delay may be a feedback regulation, as the resynthesis of IκBa is dependent on NF-κB activation.

Because NF-κB activation requires nuclear translocation of the p65 subunit of NF-κB, the cytoplasmic and nuclear pool of p65 protein was examined by western blot analysis. As shown in FIG. 5 lower panel, none of the treatments altered significantly the cytoplasmic pool of p65, but the TNF-induced appearance of p65 in the nucleus was blocked by CAPE. The decrease in the corresponding cytoplasmic pool of p65 in TNF-treated cells was not significant, perhaps because upon activation, only 20% of p65 is translocated to the nucleus.

11

EXAMPLE 8

Reducing Agents Reverse the Effect of CAPE

It has been shown that the biological effects of pervanadate, TPCK and herbimycin A on suppression of NF-κB activation can be reversed by reducing agents. Therefore, the ability of DTT, 2, 3-dimercaptopropanol (DMP), and beta mercaptoethanol (BME) to reverse the effect of CAPE was examined. Cells were treated with CAPE in the presence and absence of either DTT or DMP or BME and examined for the activation of NF-κB by TNF. As shown in FIG. 6, none of the reducing agents by themselves had a significant effect on TNF-dependent activation of NF-κB, but all reducing agents reversed completely the inhibition induced by CAPE. These results implicate the critical role of sulfhydryl groups in the TNF-dependent activation of NF-κB.

EXAMPLE 9

Structure/Activity Relationship Studies on CAPE

To delineate further the role of CAPE in inhibition of NF-κB activation, analogues of CAPE with four different types of modifications were used. These analogues included ring substituents (compounds 1, 2, 3), ester groups (compound 4), rotationally constrained variants (compounds 5 and 6), and saturated amide analogues (compound 7 and 8), all shown in FIG. 7A. These analogues have been characterized previously for their ability to inhibit human HIV integrase and cell growth (see Burke, et al., *J. Med. Chem.* 38:4171–78 (1995)). Although all the compounds were active in inhibiting NF-κB activation, there were marked variations in their inhibitory ability (FIG. 7B).

Alteration of the hydroxyl group placement from 3,4-dihydroxy pattern to 2,5-dihydroxy pattern (compound 1) increased the potency of inhibition over that resulting from replacement of the hydroxyl groups of CAPE with two methyl ethers (compound 2). However, addition of a third hydroxyl group to give 2,3,4-trihydroxy derivative (compound 3) resulted in a loss of potency, suggesting that the number and the placement of hydroxyl groups is a critical determinant of the extent of inhibition. In the group of ester analogues, the caffeic acid portion of the molecule (3,4-dihydroxycinnmic acid) was held constant and the phenylethyl side chain was varied. An increase in the length of the alkyl spacer (compound 4) resulted in a significant loss of inhibition.

In the rotationally constrained variants, bicyclic analogues of two isomers of CAPE that differed in the placement of hydroxyl substituents were used. A drastic change in the inhibitory potency of the two analogues was seen. The isomer- 5 was completely ineffective, whereas the isomer- 6 completely abolished the binding, once again indicating that the placement of the hydroxyl groups plays a critical role in inhibiting NF-κB activation.

In the saturated amide analogues, the importance of the side chain bond and the ester oxygen was examined. The analogue with three additional hydroxyls in the (phenylethyl) amine ring (compound 7) and the reverse amide analogue (compound 8), which lacked an additional hydroxyl group, were less active than CAPE. Thus, structural analogues of CAPE may be more active than CAPE (e.g., compound 6), as active as CAPE (e.g., compound 1), and less active than CAPE (e.g., compounds 2, 3, 4, 5, 7, and 8).

EXAMPLE 10

Transient Transfection and CAT Assays

HeLa cells were transiently transfected with pIκBCAT and pmutIκBCAT for 20 hours by the calcium phosphate method according to the instructions supplied by the manufacturer (GIBCO-BRL). After transfection, the medium (MEM) was replaced; cells were incubated for 24 hours at 37° C. then treated with capsaicin (300 uM) for 2 hours before stimulation with 0.1 nM TNF for 1 hour. Thereafter, cells were washed with phosphate-buffered saline and examined for CAT activity as described (Sambrook J., E. E. Fritsch, and T. Maniatis. (eds), Molecular cloning: A laboratory manual, 2d Ed. Cold Spring Harbor Press., N. Y.).

EXAMPLE 11

Capsaicin Inhibits TNF-dependent Activation of NF-κB

The effect of capsaicin and its analogue resiniferatoxin which is also structurally homologous to phorbol ester (see FIG. 8) were tested for their ability to modulate NF-κB activation. The maximum time of incubation and the concentration of the compounds used had minimal effect on cell viability or on the TNF receptors. Upon exposure of cells for 2 hours to 100 $\mu$M, 200 $\mu$M and 300 $\mu$M capsaicin, the cell viability, as determined by trypan blue exclusion, was 99%, 98% and 95%, respectively.

Figure 9A:
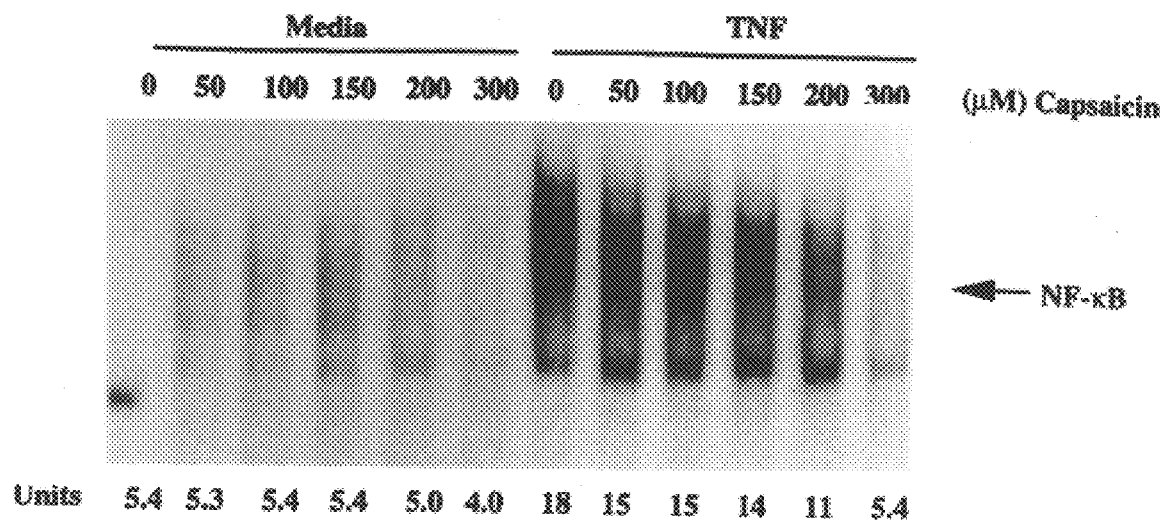

ML-1a cells were pretreated with different concentrations of capsaicin (up to 300 $\mu$M) for 2 hours, incubated either with or without TNF (0.1 nM) for 15 minutes at 37° C., and examined for NF-κB activation by electrophoretic mobility shift assays (FIG. 9A). The results show that capsaicin by itself did not activate NF-κB, and 200–300 $\mu$M capsaicin inhibited most of the activation induced by TNF. The activation of NF-κB by TNF is quite specific as the band disappeared when unlabeled oligo was added but not when the oligo with mutated binding sites was added (see FIG. 13A).

Figure 9B:
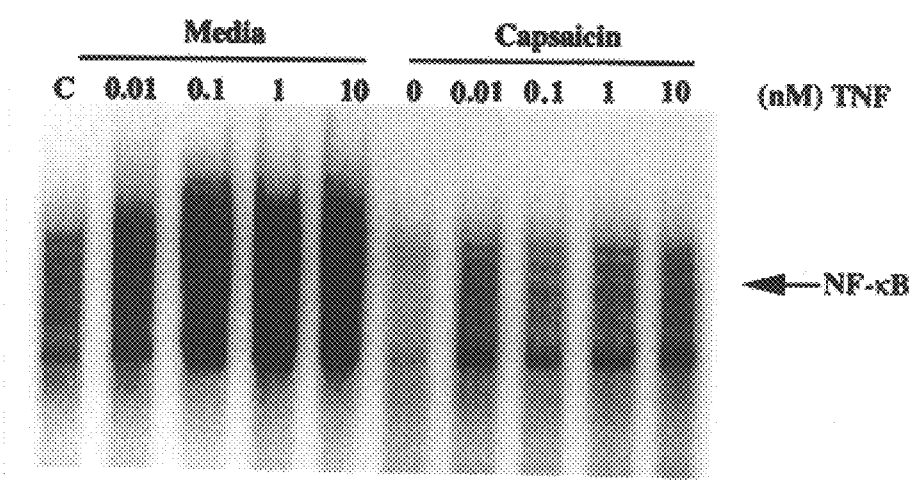

Previous studies have shown that a high concentration of TNF (10 nM) induces more robust and rapid (within 5 minutes) activation of NF-κB (Chaturvedi, et al., *J. Biol. Chem.* 269:14575–83 (1994)). To determine if capsaicin also could suppress a robust response to TNF, capsaicin-pretreated cells were challanged with increasing concentrations of TNF (up to 10 nM) for 15 minutes and then examined for NF-κB (FIG. 9B). Although the activation of NF-κB by 10 nM TNF was very strong, capsaicin completely inhibited it as efficiently as it did the 0.01 nM concentration. These results show that capsaicin is a very potent inhibitor of NF-κB activation.

Figure 9C:
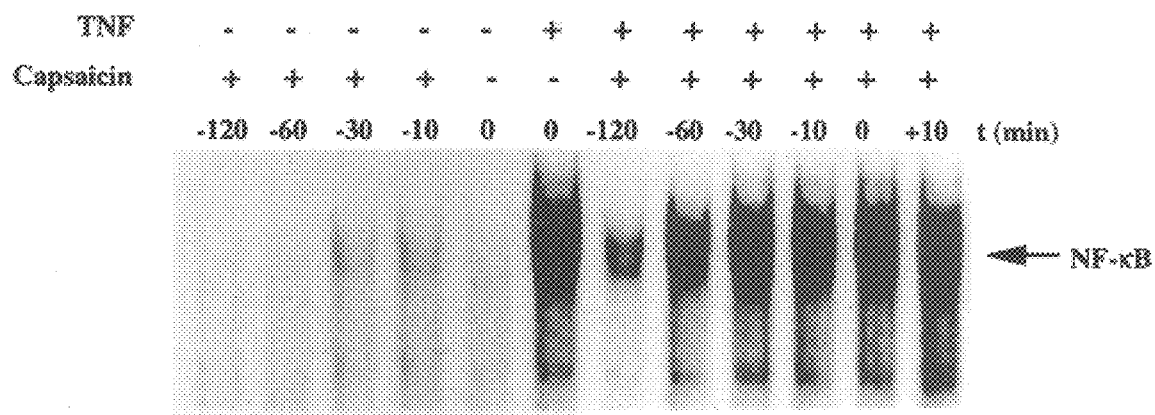

To gain further insight into the kinetics of inhibition, the cells were preincubated with capsaicin for 120, 60, 30, and 10 minutes and then exposed to TNF. Capsaicin was also added simultaneously (0 minutes) and 10 minutes after the addition of TNF. In every case, TNF was present for 30 minutes. As shown in FIG. 9C, co-incubation of cells with capsaicin and TNF together did not block NF-κB activation. The maximum inhibition of the response to TNF was noted only when cells were pre-incubated for 120 minutes with capsaicin.

EXAMPLE 12

Resiniferatoxin Also Blocks NF-κB Activation

Resiniferatoxin is a structural analogue of capsaicin and both share a common receptor (see Holzer, H. , *Pharmacol. Rev.* 43:143 (1994); and Szallasi, A., and Blumberg, P., *Brain Res.* 524:106 (1990)). Therefore, the ability of resiniferatoxin to inhibit TNF-mediated NF-κB activation was examined. Like capsaicin, treatment of cells with resiniferatoxin by itself did not activate NF-κB, but it completely inhibited TNF-mediated activation of NF-κB in a dose-dependent manner (FIG. 10). As 40 µM of resiniferatoxin was sufficient for maximum inhibition of the TNF response, it suggests that resiniferatoxin is approximately 8-fold as potent as capsaicin.

EXAMPLE 13

Activated NF-κB Inhibited by Capsaicin Consists of p50 and p65 Subunits

Various combinations of Rel/NF-κB proteins can constitute an active NF-κB heterodimer that binds to specific sequences in DNA. To show that the retarded band visualized by electrophoretic mobility shift assays in TNF-treated cells was indeed NF-κB, nuclear extracts from TNF-activated cells were incubated with antibody to either p50 (NF-κB1) or p65 (Rel A) subunits and electrophoretic mobility shift assays were performed. Antibodies to either subunit of NF-κB shifted the band to a higher molecular weight (FIG. 11A), thus suggesting that the TNF-activated complex consists of both the p50 and p65 subunits. A partial shift noted with anti-p65 antibody may be due to the nature of the antibodies or the conditions used. As a control, an unrelated antibody (NS) was run; it had no effect on the NF-κB bands.

It has been shown that both TPCK, a serine protease inhibitor, and herbimycin A, a protein tyrosine kinase inhibitor, downregulate NF-κB activation by chemical modification of the NF-κB subunits thus preventing NF-κB's binding to DNA. To determine if capsaicin directly modifies NF-κB proteins, DNA was incubated with either deoxycholate-treated cytoplasmic extracts from capsaicin-exposed cells (FIG. 11B) or nuclear extracts exposed to capsaicin after TNF treatment (FIG. 11C) and electrophoretic mobility shift assays were performed. The deoxycholate treatment has been shown to dissociate the IκBa subunit, thus releasing NF-κB for binding to the DNA. The results in FIGS. 11B and 11C show that capsaicin did not modify the ability of NF-κB to bind to the DNA. Therefore capsaicin inhibits NF-κB activation through a mechanism different from that of TPCK or herbimycin A.

EXAMPLE 14

Capsaicin Also Blocks NF-κB Activation Induced by Other Agents

Figure 12A:
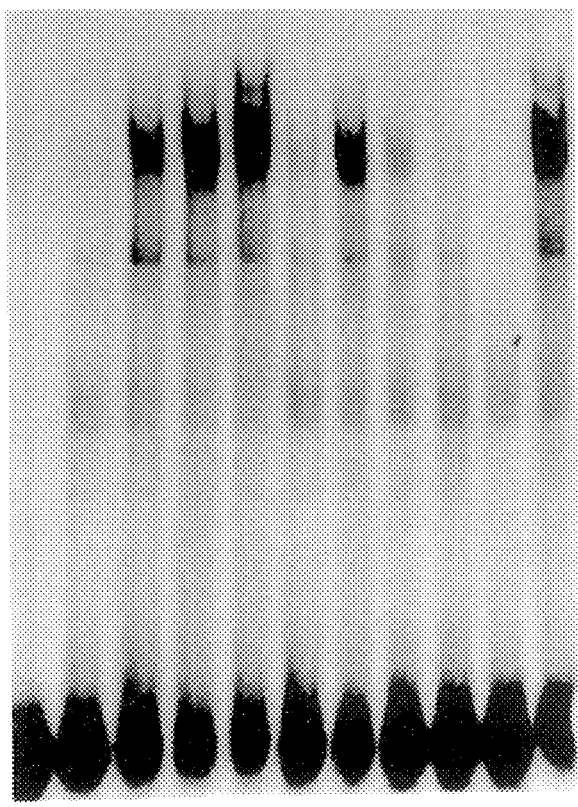

NF-κB activation is induced by a wide variety of other agents including TNF, phorbol myristate acetate and okadaic acid. However, it was not clear whether the pathway leading to the NF-κB activation is same for all these agents. Therefore, the effect of capsaicin on the activation of NF-κB by different agents was examined. Like TNF, capsaicin completely blocked phorbol myristate acetate-induced activation of NF-κB, but activation mediated through okadaic acid was inhibited only partially (FIG. 12A).

EXAMPLE 15

Inhibition of NF-κB Activation by Capsaicin is not Cell Type Specific

Besides ML-1a cells, the ability of capsaicin to block TNF-mediated NF-κB activation in other myeloid (U-937) and epithelial (HeLa) cells was examined. The result of these experiments, shown in FIG. 12B, indicate that capsaicin inhibited TNF-induced NF-κB in both of these cell types. Almost complete inhibition was noted at 200 µM capsaicin, thus suggesting that this effect of capsaicin is not cell type specific.

EXAMPLE 16

Capsaicin Inhibits TNF-dependent Degradation of IκBa

It has been shown that upon stimulation of cells, IκBa is phosphorylated and undergoes proteolytic degradation, thus allowing NF-κB to translocate to the nucleus. It was a goal of the present invention to determine whether the inhibitory action of capsaicin was due to prevention of IκBa degradation. The cytoplasmic levels of IκBa protein were examined by western blot analysis. The results shown in FIG. 13A indicate that TNF treatment of cells caused the appearance of a slower-migrating band of IκBa within 5 minutes; and by 15 minutes IκBa completely disappeared (upper panel). The pretreatment of cells with capsaicin, however, abolished both the appearance of TNF-mediated slower-migrating band as well as degradation of IκBa (lower panel). The appearance of the slower-migrating band has been shown to be induced by phosphorylation of IκBa at serine 32 and 36 (see Finco, et al., *Proc. Natl. Acad. Sci. U.S.A.* 91:11884–88 (1994)).

Figure 13A:
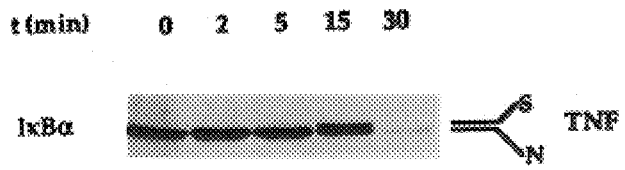
Figure 13B:
Figure 13B:
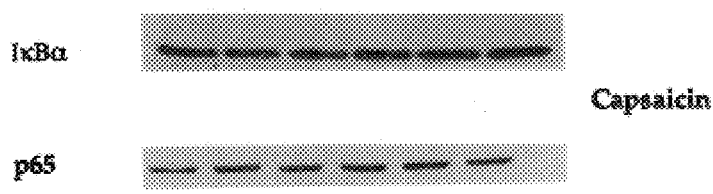

The level of p65 and IκBa in the cytoplasm of cells treated with capsaicin for different times was investigated (FIG. 13B). The levels of cytoplasmic IκBa (upper panel) and p65 (lower panel) remained unaffected in capsaicin-treated cells. However, when the level of p65 in the cytoplasm and nucleus of cells treated with capsaicin alone or with TNF and capsaicin together or with only TNF was examined, it was found that TNF induced the migration of p65 protein into the nucleus. Capsaicin by itself did not induce this migration but it did block the TNF-induced migration. These results indicate that capsaicin does not affect the level of p65 but rather prevents its TNF-dependent translocation to the nucleus. In addition to p65, the effect of capsaicin was also examined on the cytoplasmic pool of other members of the Rel family of proteins. The results shown in FIG. 13D indicate that neither capsaicin by itself or in combination with TNF had any effect on the levels of either p50 or c-Rel proteins.

EXAMPLE 17

Capsaicin Represses the IκBa -CAT Gene Expression

As the promoter of the IκBa gene has NF-κB binding sites and is regulated upon NF-κB activation inducing within minutes rapid gene expression, a transient-expression assay was used to determine the effect of capsaicin on the TNF-induced IκBa promoter linked to the CAT gene. As expected, almost four-fold increase in CAT activity was obtained upon stimulation with TNF (FIG. 14). However, TNF-enhanced CAT activity was reduced significantly when pIκBCAT-transfected cells were pretreated with capsaicin for 2 hours prior to TNF treatment. Transfection with an IκB promoter containing a mutated NF-κB binding site, pmutIκBCAT, did not result in induction of CAT by TNF. These results demonstrate that capsaicin can also repress the gene expression induced by NF-κB activator.

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes to this invention and other uses will occur to those skilled in the art which are encompassed within the spirit of the invention as defined by the scope of the claims.

What is claimed is:

1. A method of inhibiting the activation of nuclear transcription factor NF-κB in cells in vitro or in vivo, comprising the step of treating said cells with caffeic acid phenethyl ester (CAPE).

2. The method of claim 1, wherein said activation of NF-κB is induced by an agent selected from the group consisting of tumor necrosis factor, phorbol ester, ceramide, okadaic acid, and hydrogen peroxide.

3. A method of inhibiting the activation of nuclear factor NF-κB in cells in vitro or in vivo, comprising the step of treating said cells with an agent selected from the group consisting of a 2,5-dihydroxy analogue of CAPE, a 5,6-dihydroxy bicyclic analogue of CAPE, 8-methyl-N-vanillyl-6-nonenamid (capsaicin), and resiniferatoxin.

* * * * *

UNITED STATES PATENT AND TRADEMARK OFFICE
CERTIFICATE OF CORRECTION

PATENT NO. : 5,981,583
DATED : November 9, 1999
INVENTOR(S) : Bharat B Aggarwal and Dezider Grunberger It is certified that error appears in the above-identified patent and that said Letters Patent is hereby corrected as shown below:

In Column 1, line 54, please insert a comma after "et al."

In Column 1, line 61, "e. g." should read --e.g.--.

In Column 2, lines 18, "et al. ," should read --et al.,--.

In Column 2, line 29, "In vitro" should read --*In vitro*--.

In Column 2, line 38, please insert a comma after "et al."

In Column 3, line 54, "1B upper panel:" should read --FIG. 1B-1:--

In Column 3, line 61, "1B lower panel:" should read --FIG. 1B-2--.

Figure 2A:
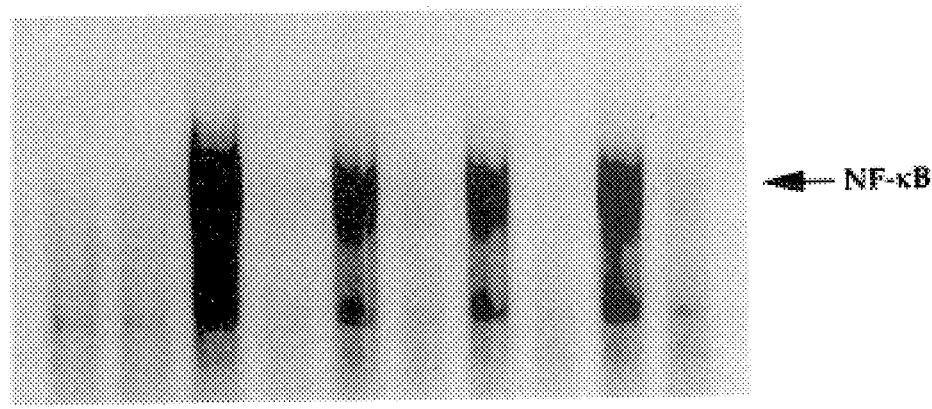

In Column 4, line 11, please insert the words --(FIG. 2A)-- between the words "activation." and "The".

Figure 2B:
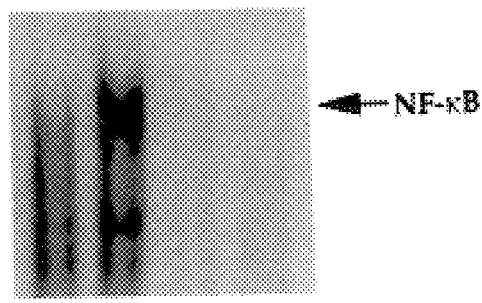

In Column 4, line 13, please insert the words --(FIG. 2B-- after the word "others."

In Column 4, line 15, please delete the period after the word "3A" and replace it with a comma.

UNITED STATES PATENT AND TRADEMARK OFFICE
CERTIFICATE OF CORRECTION

PATENT NO. : 5,981,583
DATED : November 9, 1999
INVENTOR(S) : Bharat B Aggarwal and Dezider Grunberger It is certified that error appears in the above-identified patent and that said Letters Patent is hereby corrected as shown below:

In Column 4, line 18, please insert a comma after the words "3B".

Figure 5A:
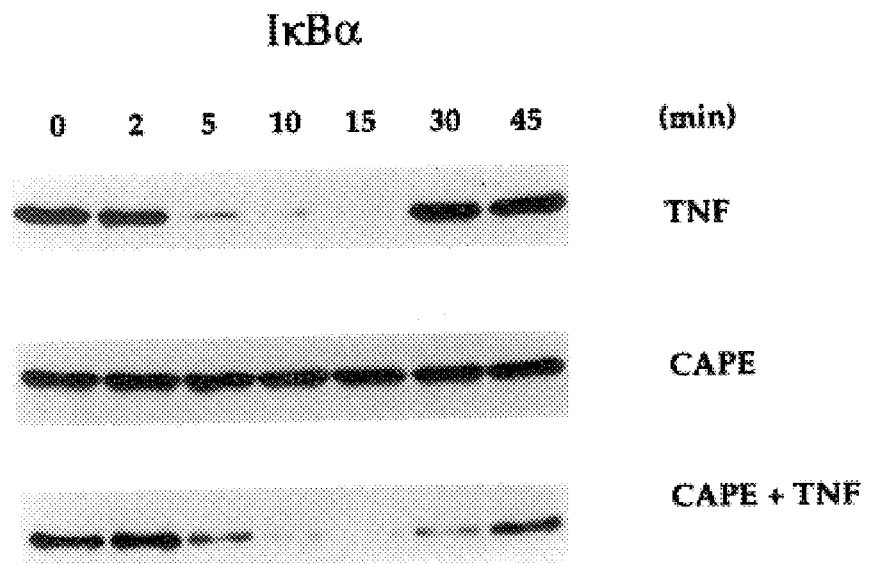

In Column 4 line 32, "(upper panel)" should read --FIG. 5A--.

Figure 5B:
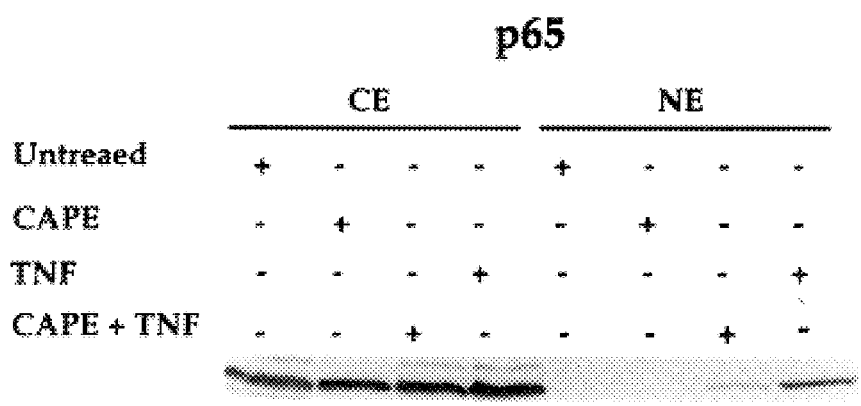

In Column 4, line 32, "(lower panel)" should read --FIG. 5B--.

In Column 4, line 40, "($2 \times 10^{6}$/ml)" should read --($2 \times 10^{6}$/ml)--.

In Column 4, line 47, "(7B)" should read --(7B-1 & 7B-2)--.

In Column 4, line 49, "(upper panel)" should read --FIG. 7B-1--.

In Column 4, line 49, "(lower panel)" should read --FIG. 7B-2--.

In Column 4, line 56, please insert the words --(FIG. 8A)-- after the word "capsaicin".

In Column 4, line 56, please insert the words --(FIG. 8B)-- after the word "resiniferatoxin".

In Column 4, line 56, please insert the words --(FIG. 8C)-- after the word "acetate".

UNITED STATES PATENT AND TRADEMARK OFFICE
CERTIFICATE OF CORRECTION

PATENT NO. : 5,981,583
DATED : November 9, 1999
INVENTOR(S) : Bharat B Aggarwal and Dezider Grunberger Page 3 of 5

It is certified that error appears in the above-identified patent and that said Letters Patent is hereby corrected as shown below:

In Column 4, line 57, "reseutls" should read --results--.

In Column 4, line 61, "9A:" should read --FIG. 9A--.

In Column 4, line 64, "9B" should read --FIG. 9B--.

In Column 5, line 1, "9C" should read --FIG. 9C--.

Figure 11A:
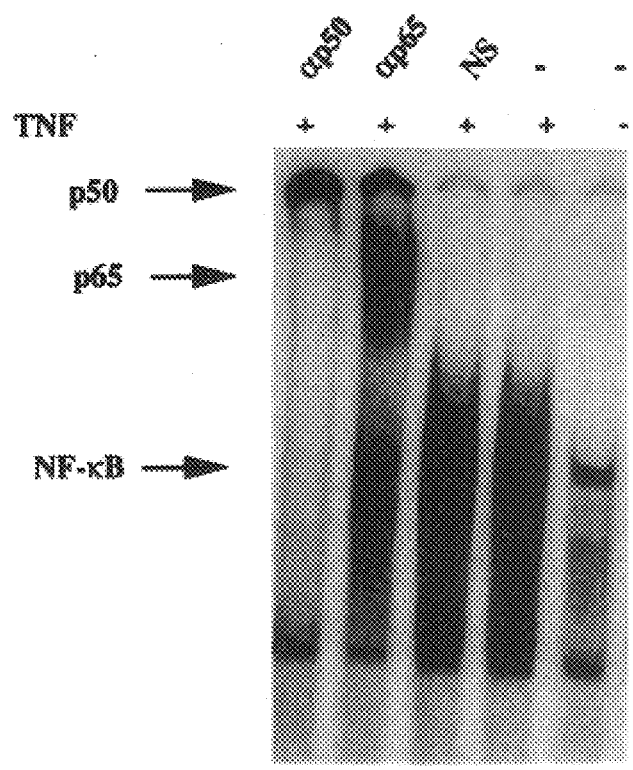
Figure 11B:
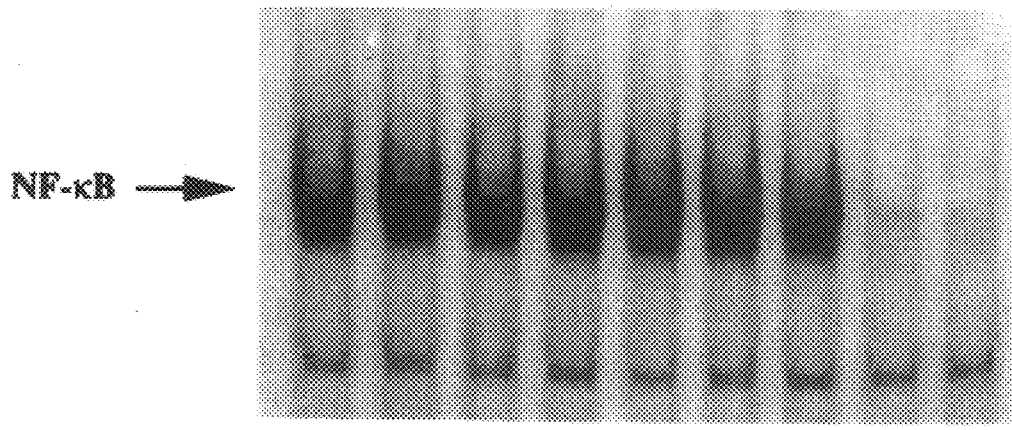
Figure 11C:
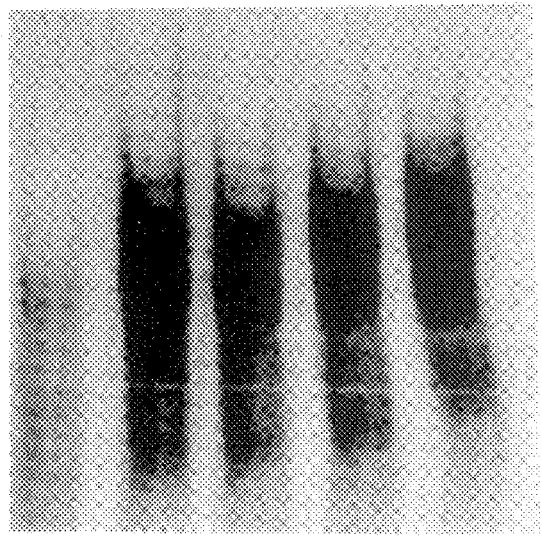

In Column 5, line 17, "FIG. 11" should read --FIG. 11A--.

In Column 5, line 21, "panel (A)" should read --FIG. 11B--.

In Column 5, line 26, "panel (C)" should read --FIG. 11C--.

In Column 5, line 32, "panel 12A" should read --FIG. 12A--.

Figure 12B:
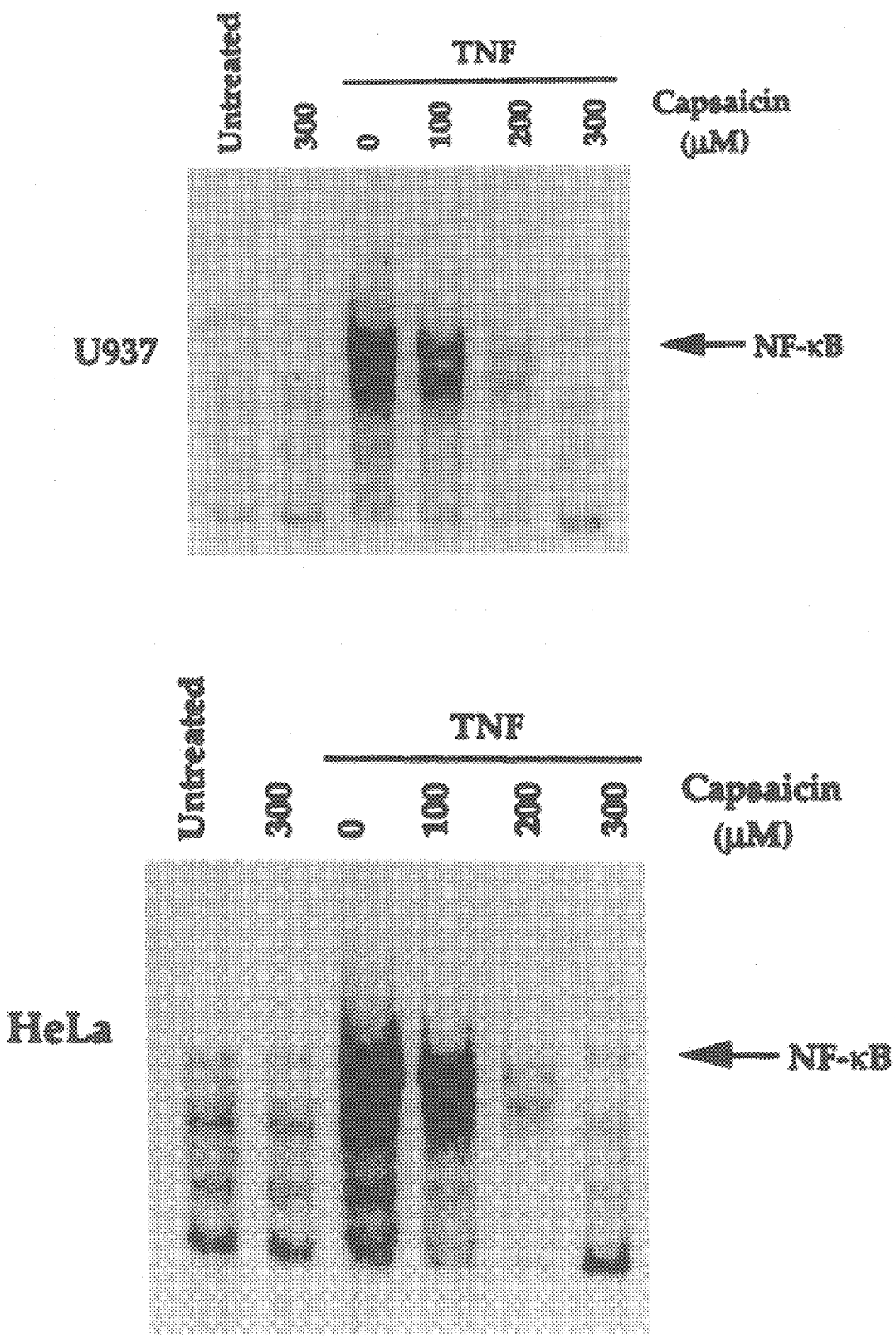

In Column 5, line 40, "panel 12B" should read --FIG. 12B--.

In Column 5, line 47, "13A" should read --FIG. 13A--.

In Column 5, line 53, "13B" should read --FIG. 13B--.

Figure 13C:
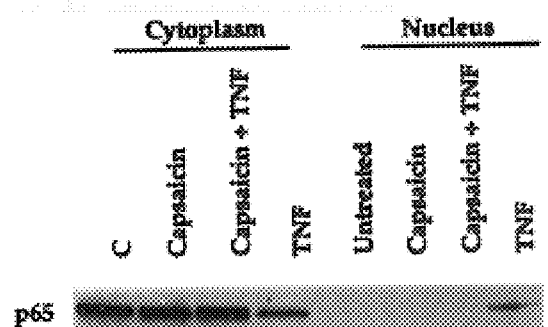

In Column 5, line 56, "13C" should read --FIG. 13C--.

UNITED STATES PATENT AND TRADEMARK OFFICE
CERTIFICATE OF CORRECTION

Figure 13D:
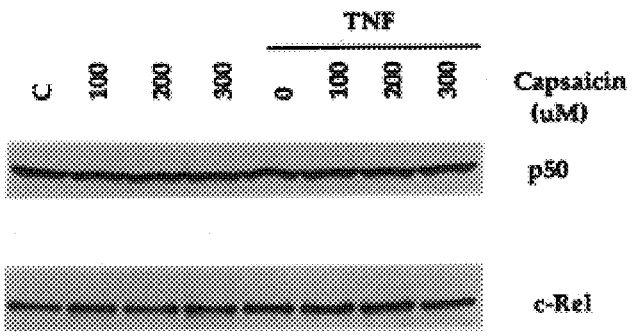

PATENT NO. : 5,981,583
DATED : November 9, 1999
INVENTOR(S) : Bharat B Aggarwal and Dezider Grunberger It is certified that error appears in the above-identified patent and that said Letters Patent is hereby corrected as shown below:

In Column 5, line 61, "13D" should read --FIG. 13D--.

In Column 7, line 40, please insert a comma after the words "et al.".

In Column 9, line 46, "(FIG. 1B. upper panel)" should read --FIG. 1B--.

In Column 9, line 55, "(FIG. 1B. upper panel)" should read --FIG. 1B--.

In Column 9, line 62, "(FIG. 1B. lower panel)" should read --FIG. 2--.

In Column 10, line 5, "b y" should read --by--.

In Column 10, line 16, "not" should read --Not--.

Figure 3A:
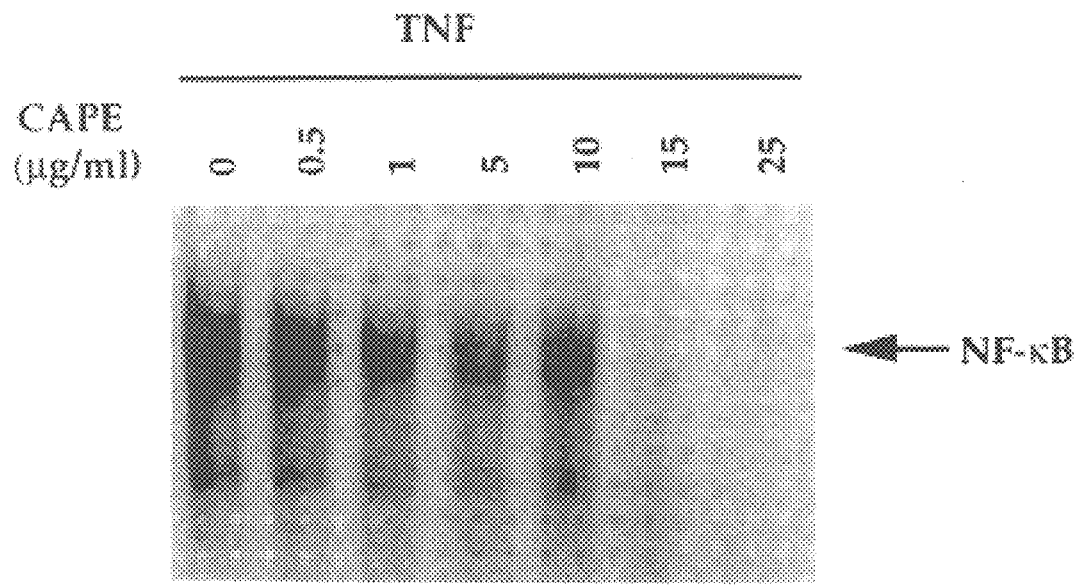

In Column 10, line 25, "(FIG. 3. upper panel)" should read --FIG. 3A--.

Figure 3B:
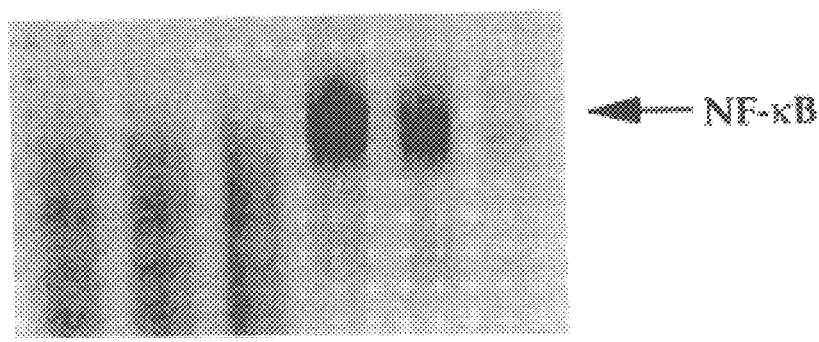

In Column 10, line 33, "(FIG. 3 lower panel)" should read --FIG. 3B--.

In Column 10, line 49, "FIG. 5 upper panel" should read --FIG. 5A--.

In Column 10, line 61, "FIG. 5 lower panel" should read --FIG. 5B--.

UNITED STATES PATENT AND TRADEMARK OFFICE
CERTIFICATE OF CORRECTION

PATENT NO. : 5,981,583
DATED : November 9, 1999
INVENTOR(S) : Bharat B Aggarwal and Dezider Grunberger It is certified that error appears in the above-identified patent and that said Letters Patent is hereby corrected as shown below:

In Column 11, line 29, "(FIG. 7B)" should read -- FIGS. 7B-1 & 7B-2--.

In Column 12, lines 19-20, please delete the words "(see FIG. 8)".

In Column 13, line 61, "is not" should read --Is Not--.

Signed and Sealed this

Twenty-second Day of May, 2001

Attest:

NICHOLAS P. GODICI

Attesting Officer    Acting Director of the United States Patent and Trademark Office